(12) United States Patent
Sim (10) Patent No.: US 11,759,232 B2
(45) Date of Patent: Sep. 19, 2023

(54) NEEDLE GUIDE TEMPLATE FOR PERIRECTAL SPACER AND FIDUCIAL MARKER PLACEMENT

(71) Applicant: Sang E Sim, Allendale, NJ (US)

(72) Inventor: Sang E Sim, Allendale, NJ (US)

( * ) Notice: Subject to any disclaimer, the term of this patent is extended or adjusted under 35 U.S.C. 154(b) by 0 days.

(21) Appl. No.: 17/687,993

(22) Filed: Mar. 7, 2022

(65) Prior Publication Data
US 2022/0287794 A1 Sep. 15, 2022

Related U.S. Application Data

(60) Provisional application No. 63/160,846, filed on Mar. 14, 2021.

(51) Int. Cl.
*A61B 17/34* (2006.01)
*A61B 90/00* (2016.01)

(52) U.S. Cl.
CPC .......... *A61B 17/3403* (2013.01); *A61B 90/39* (2016.02); *A61B 2017/3411* (2013.01); *A61B 2090/3908* (2016.02); *A61B 2090/3983* (2016.02); *A61B 2090/3987* (2016.02)

(58) Field of Classification Search
CPC ........ A61B 17/3403; A61B 2017/3411; A61B 2090/3987
See application file for complete search history.

(56) References Cited

U.S. PATENT DOCUMENTS

| | | | | |
|---|---|---|---|---|
| 5,931,786 | A * | 8/1999 | Whitmore, III | A61N 5/1007 600/459 |
| 6,036,632 | A * | 3/2000 | Whitmore, III | A61N 5/1007 604/116 |
| 6,206,832 | B1 * | 3/2001 | Downey | A61B 17/3403 600/7 |
| 6,500,109 | B2 * | 12/2002 | Tokita | A61N 5/1007 604/116 |
| 11,464,499 | B2 * | 10/2022 | Coakley | A61B 10/0241 |
| 2021/0016104 | A1 * | 1/2021 | Cavanaugh | A61N 5/1007 |

* cited by examiner

*Primary Examiner* — Angela M Hoffa
*Assistant Examiner* — Younhee Choi (57) ABSTRACT

A template grid which attaches to an ultrasound stepper of a transrectal ultrasound unit providing transperineal guidance and support through adjustable angle apertures allowing for accurate targeting of a medical implant such as a needle to its intended target such as for purposes of perirectal spacer placement. The rotational apertures allow for free adjustable changes in the trajectory of a medial implant such as a needle to its intended target while providing stability and support to the medical implant itself. The template grid, in addition, contains fixed apertures for placement of a medical implant such as a needle into the substance of the prostate gland positioned to avoid inadvertent passage through the urethra and rectum.

8 Claims, 10 Drawing Sheets

NEEDLE GUIDE TEMPLATE FOR PERIRECTAL SPACER AND FIDUCIAL MARKER PLACEMENT

CROSS REFERENCE TO RELATED APPLICATIONS

The present application claims priority to the earlier filed provisional application having Ser. No. 63/160,846 and hereby incorporates subject matter of the provisional application in its entirety.

FIELD

The present invention relates to the field of interventional urologic procedures, specifically devices, and methods of passing a medical implant through the perineum utilizing an endorectal ultrasound and ultrasound stepper unit.

BACKGROUND

Radiation therapy is an accepted and standard treatment of prostate cancer. Prior to delivery of treatment, fiducial marker placement consisting of inert radio-opaque pellets or seeds are commonly placed in the substance of the prostate gland for purposes of image guidance of radiation treatment delivery. Thereby, the seeds would serve as radiographically visible surrogates for proper aiming of the intended target, the prostate gland. In addition, a hydrogel system (SPACEOAR system, Boston Scientific) has been developed and utilized to separate the rectum from the prostate gland with purposes of reducing radiation doses to the rectum and thereby reducing risks of injury. The hydrogel system is commercially available and widely utilized. These two procedures can and often are performed during a single procedure.

Placement of fiducial seeds transperineally can be performed with or without a template grid. A template grid would help to stabilize and maintain a common trajectory for each needle placed thereby reducing risks of inadvertent passage of each needle through normal critical tissue including rectum and urethra.

Placement of a hydrogel spacer is placed transperineally utilizing ultrasound guidance typically without a template or stabilization system as none exists thus far for this purpose. Standardly utilized commonly available grids used to guide placement of needles consists of a block of plastic or metal with multiple apertures spaced at 5 mm intervals both vertically and horizontally. These grids allow for controlled trajectory of needle placement perpendicular to the plane of the grid. They would typically not be suitable for placement of this hydrogel as the trajectory of the needle would need to be adjustable within the grid.

The procedure of placement of hydrogel spacer (SpaceOAR) requires an 18 gauge needle to be placed through the perineal skin and guided utilizing both sagittal and axial view of an endorectal ultrasound. Commonly, the angle/trajectory of the needle is adjusted to facilitate accurate placement. The posterior surface of the prostate and anterior rectum lie adjacent to each other and are separated only by Denonvilliere's fascia, a thin space between these two organs. The needle tip must accurately be placed in this space without penetrating the rectum or prostate. With the needle tip in proper position, sterile injectable saline is inserted with a syringe to hydrodissect a larger space between these two organs. Following this, the saline syringe must be detached and the hydrogel syringe must be attached while ensuring the needle tip does not move from its critical position as any migration of the needle tip could permit misplacement of the hydrogel. Without a template with stabilization, this technique is performed "free hand".

Currently, template grid systems exist that provide several fixed apertures which facilitate passage of a medical implant (e.g. needles, catheters) into the perineum utilizing a fixed trajectory. Techniques of adjusting the angle of these fixed template grid systems have also been established. However, nothing currently exists that permits movement of the medical implant to facilitate adjusting the trajectory of the implant for proper position to its intended target while maintaining the stability of the medical implant itself.

SOME EXAMPLES EMBODIMENTS

A system in accordance with the embodiment may provide adjustable apertures to allow for maneuverability of a needle to be placed accurately by adjusting the trajectory of its path. Thus, this would permit the movement of the medical implant while significantly improving stabilization to reduce the risk of misplacement and possible injury.

A system in accordance with the embodiment may include a grid system that consists of central midline (left to right) apertures which facilitate passage of a medical implant (e.g. needles, catheters) into the perineum and which allow a variable nonfixed trajectory of the medical implant to facilitate accurate and proper positioning to its intended target. These apertures allow for maneuverability of a medical implant to be placed accurately by adjusting the angle of the needle path. In addition, the grid system may consist of several fixed apertures which facilitate passage of a medical implant (e.g. needles, catheters) into the perineum utilizing a fixed trajectory. These apertures may be placed laterally and anteriorly away from the anatomic position of the urethra which lies midline and the rectum that lies posteriorly. This ensures the safe passage of needles avoiding these critical structures minimizing injury risks.

The current invention would benefit the medical provider in passing medical implants such as needles or catheters through the perineum to specific intended targets when utilizing an endorectal ultrasound and ultrasound stepper unit by allowing adjustment of the angle of trajectory. It would assist medical providers to adjust and maintain proper position of the needle tip to minimize inadvertent migration and subsequent misplacement and potential injury risks by providing stabilization of the needle in such procedures such as perirectal spacer placement. In addition, the current invention would benefit those who perform fiducial marker placement by providing fixed apertures which traject away from the urethra and rectum to minimize inadvertent puncture to these organs.

BRIEF DESCRIPTION OF THE DRAWINGS

An exemplary embodiment is illustrated by way of example, and not by way of limitation, in the figures in which like reference numerals refer to similar elements.

DESCRIPTION OF SOME EMBODIMENTS

The template grid and methods provided herein allow for placement of a medical implant such as a needle or catheter to be placed, in conjunction with an endorectal ultrasound and ultrasound stepper unit, through the perineum and its angle of trajectory to be adjusted real time by maneuvering the medical implant through an adjustable aperture which allows rotational movement. The adjustment of the trajectory is performed by maneuvering the medical implant itself free of other adjustment devices such as knobs, wheels, or levers. The template grid also provides fixed trajectory apertures for safe passage of needles into the substance of the prostate gland positioned laterally and anteriorly away from the urethra and rectum, respectively.

Referring now to the drawing figures in which like reference designators refer to like elements, there is shown in FIGS. 1, 2, 3, and 4, a template grid complete according to the present invention. The template grid has a series of passages, 6-17, that extend from front, FIG. 1 through the back, FIG. 2. Passages 6-17 are sized to accomodate a medical implant such as needles. Passages 6-17 are arranged in a pattern to allow for options of placement of a medical implant into the substance of the prostate gland anteriorly to avoid the rectum and laterally to avoid the urethra which anatomically lies midline, left to right. Passages 6-17 are fixed trajectory apertures allowing a medical implant such as needles to pass perpendicular to the front surface of the template grid. The space above and below the template may purposefully be left void to leave options for freehand medical implant placement.

Passages 19 and 20 are also sized to accommodate a medical implant such as needles. However, passages 19 and 20 allow for rotational adjustment to alter the trajectory of the medical implant. This allows for a medical implant to be placed more precisely with variable angles to approach a more precise position such as the space between prostate and rectum for perirectal spacer placement. The overall dimensions of the invention are 8.1 cm×5.9 cm×1.0 cm as demonstrated in FIG. 11.

Support rods 3 and 4 are placed along the lower surface of the template grid and will allow attachment to an ultrasound stepper unit for stabilization of the unit. In this regard, U.S. Pat. No. 5,931,786A, the contents which are incorporated herein by reference, discloses the endorectal ultrasound stepper system and mounting description of a template grid.

Figure 5:
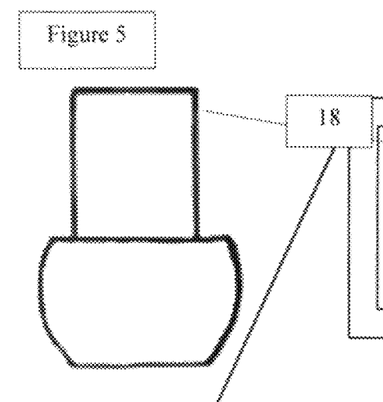
FIG. 5: Ball unit side view
Figure 6:
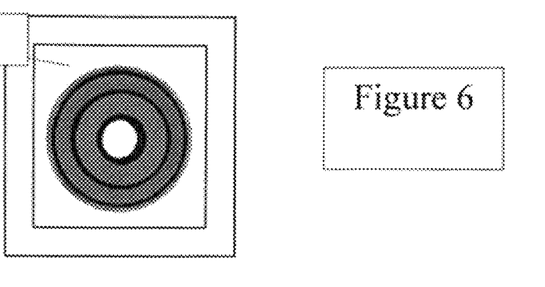
FIG. 6: Ball unit front view displaying central aperture for medical implant (needle, catheter)
Figure 7:
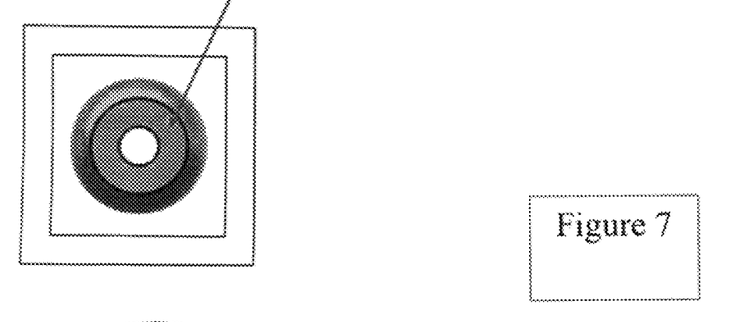
FIG. 7: Ball unit rear view displaying central aperture for medical implant (needle, catheter)

The construction of apertures 19 and 20 are a ball and joint configuration. FIGS. 5, 6, and 7 demonstrated item 18 which is the rotational part with a central aperture 19 and 20 within it. FIG. 5 is view of the ball unit from a sagittal (side) view. FIG. 6 is a cross view of the ball unit from the stem side of the unit. FIG. 7 is a cross view of the ball unit from the ball side of the unit. The ball end of item 18 in FIGS. 5, 6, and 7 rotate within the socket labeled 1 and 2 of the template in FIG. 8.

This allows a needle to be place through the passage in 19 and 20 and rotate to allow for variable angle of entry for adjustable trajectory to facilitate accurate placement of a medical implant. The stem portion of the ball unit prevents the aperture from rolling away into the body of the template and away from access of a medical implant.

Figures 9, 10:
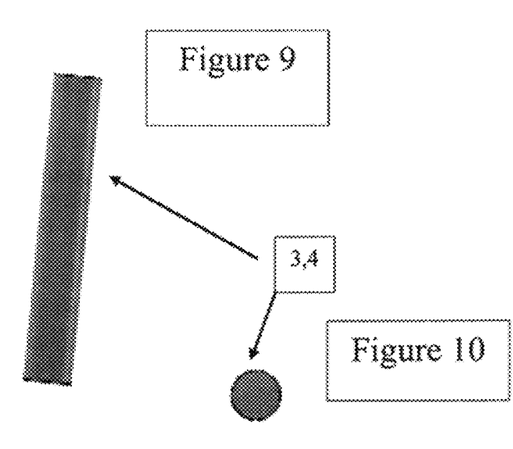
FIG. 9: Support rod for attachment to an ultrasound stepper unit, side view
FIG. 10: Support rod for attachment to an ultrasound stepper unit, cross sectional view

Support rods 3 and 4 are cylindrical solid supports shown in FIGS. 9 and 10. They are placed along the bottom surface of the template grid body as demonstrated in FIGS. 1, 2, 3, and 4. These rods serve to mount and fix to an endorectal ultrasound stepper. In this regard, U.S. Pat. No. 5,931,786A, the contents which are incorporated herein by reference, discloses the endorectal ultrasound stepper system and mounting description of a template grid.

Figure 11:
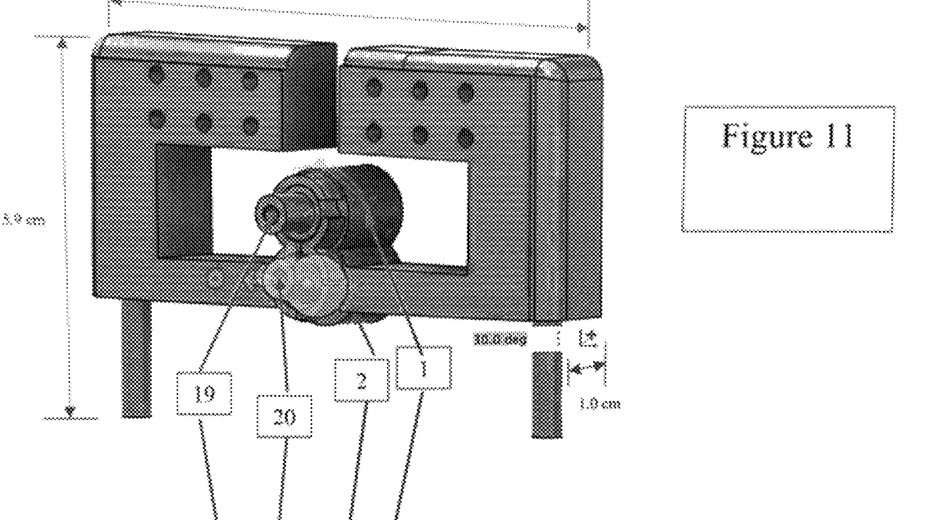
FIG. 11: Template system demonstrating lower variable aperture with needle path angling down. Figure also demonstrates the size of the overall embodiment as 8.1 cm×5.9 cm×1.0 cm.
Figure 12:
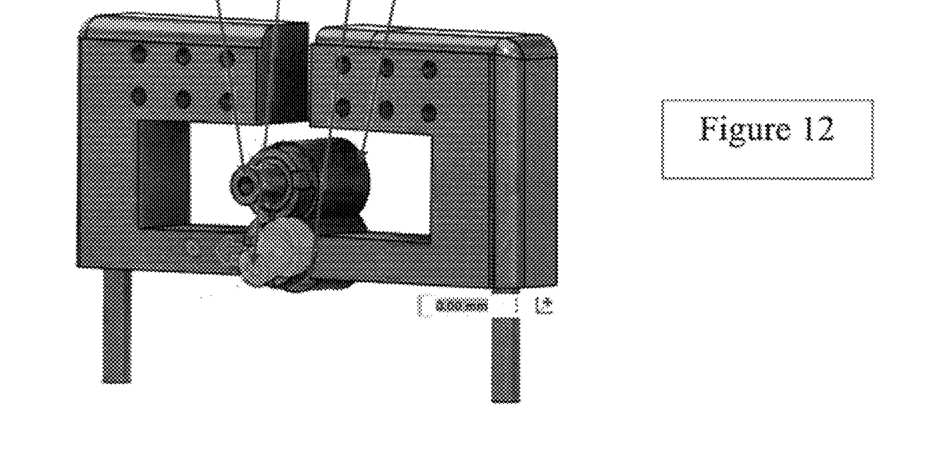
FIG. 12: Template system demonstrating lower variable aperture with needle path angling up

FIG. 11 demonstrates the lower aperture 20 with a slightly upward position. In contrast, FIG. 12 demonstrates the lower aperture 20 now in a downward position. With the ability to rotate the aperture, this allows the medical implant trajectory to be freely altered to facilitate precise placement of the medical implant. The size of this example of the current invention device is demonstrated on FIG. 11 as 8.1 cm×5.9 cm×1.0 cm. The size of other iterations of this invention may be variable depending on position of both rotational and fixed apertures.

Figure 13:
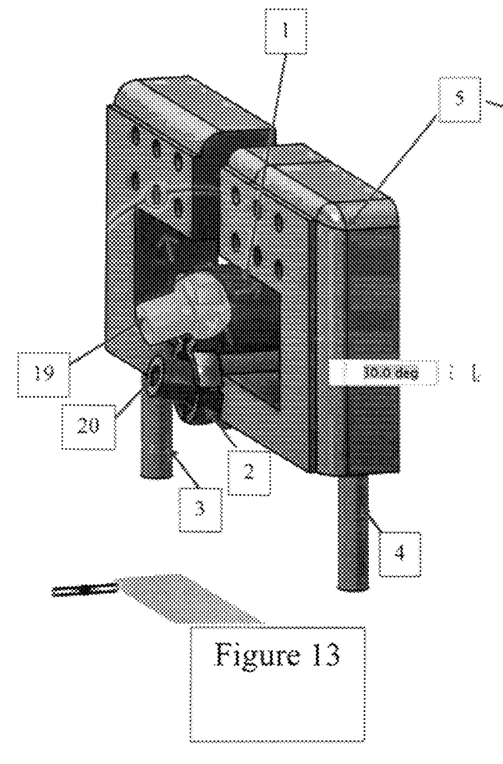
FIG. 13: Template system demonstrating upper variable aperture with needle path angling up
Figure 14:
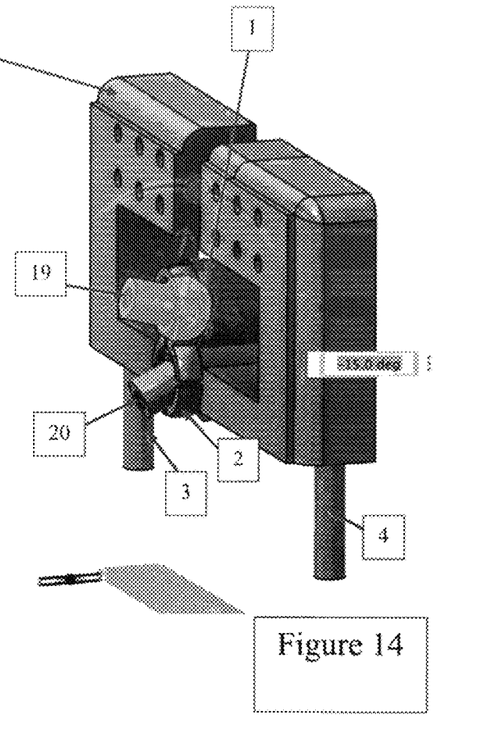
FIG. 14: Template system demonstrating upper variable aperture with needle path angling down
Figure 15:
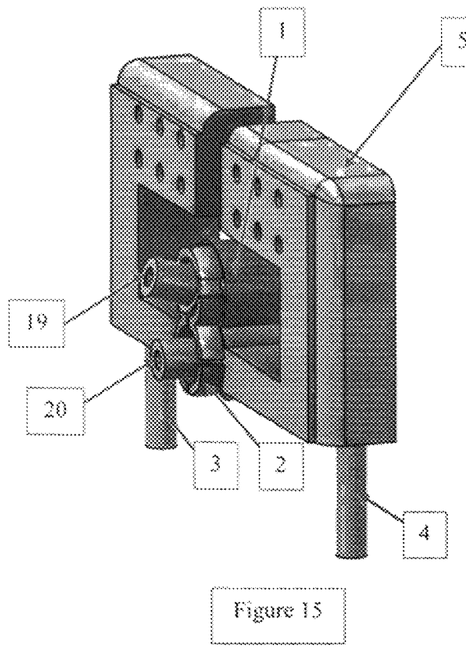
FIG. 15: Template system demonstrating upper variable aperture with needle path angling down and lower variable aperture with needle path angling straight (neutral).
Figure 16:
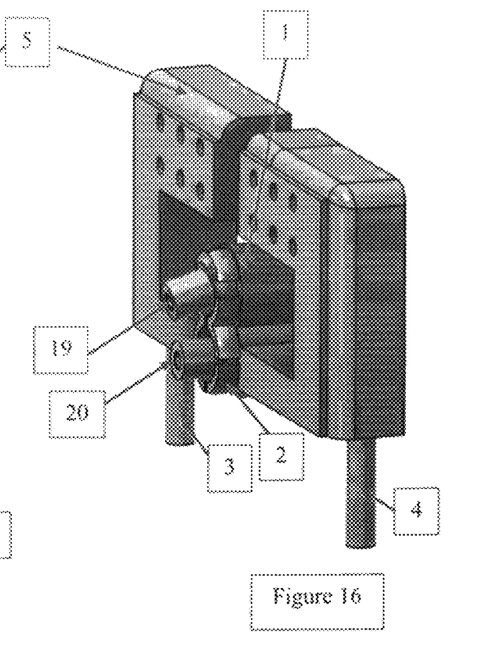
FIG. 16: Template system demonstrating upper variable aperture with needle path angling up and lower variable aperture with needle path angling straight (neutral).
Figure 17:
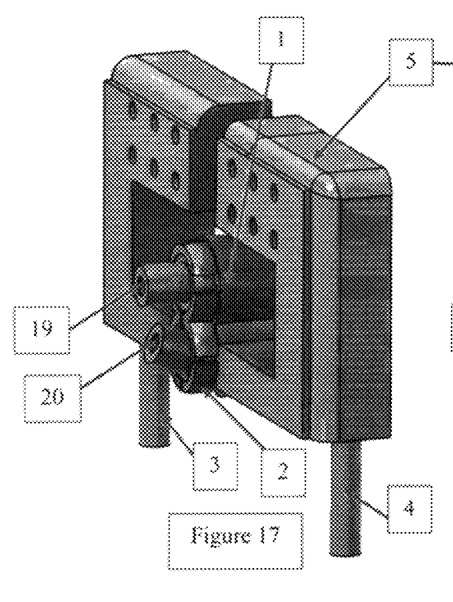
FIG. 17: Template system demonstrating upper variable aperture with needle path angling straight (neutral) and lower variable aperture with needle path angling down.
Figure 18:
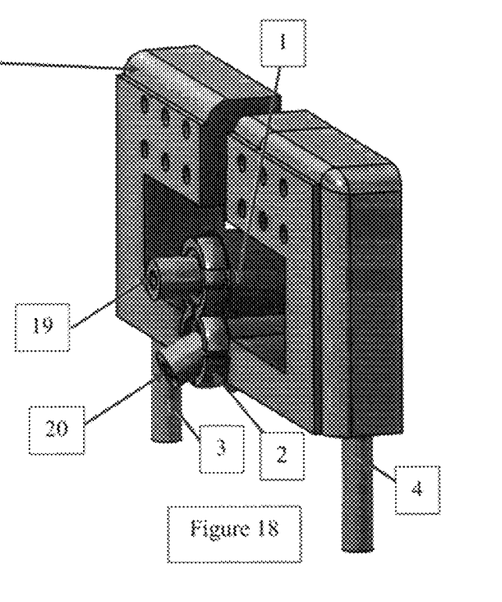
FIG. 18: Template system demonstrating upper variable aperture with needle path angling straight (neutral) and lower variable aperture with needle path angling up.

FIGS. 13 and 14 demonstrate similar rotational ability of the upper aperture 19 with FIG. 13 demonstrating the aperture pointing downwards and FIG. 14 demonstrating the aperture pointing upwards.

FIGS. 15, 16, 17, and 18 demonstrate the template grid complete according to the present invention with apertures 19 and 20 in different positions to further demonstrate the variability and maneuverability of the upper and lower apertures.

The template grid represented in FIGS. 1, 2, 3, and 4 can be made by any suitable material. The template grade can be made to be reusable or disposable. In this regard, U.S. Pat. No. 6,036,632, the contents of which are incorporated herein by reference, discloses disposable template grid systems. The template grid system can be sterilized by a method compatible of the material it is produced with and may include options of steam sterilization, gas sterilization, or irradiation.

Figure 19:
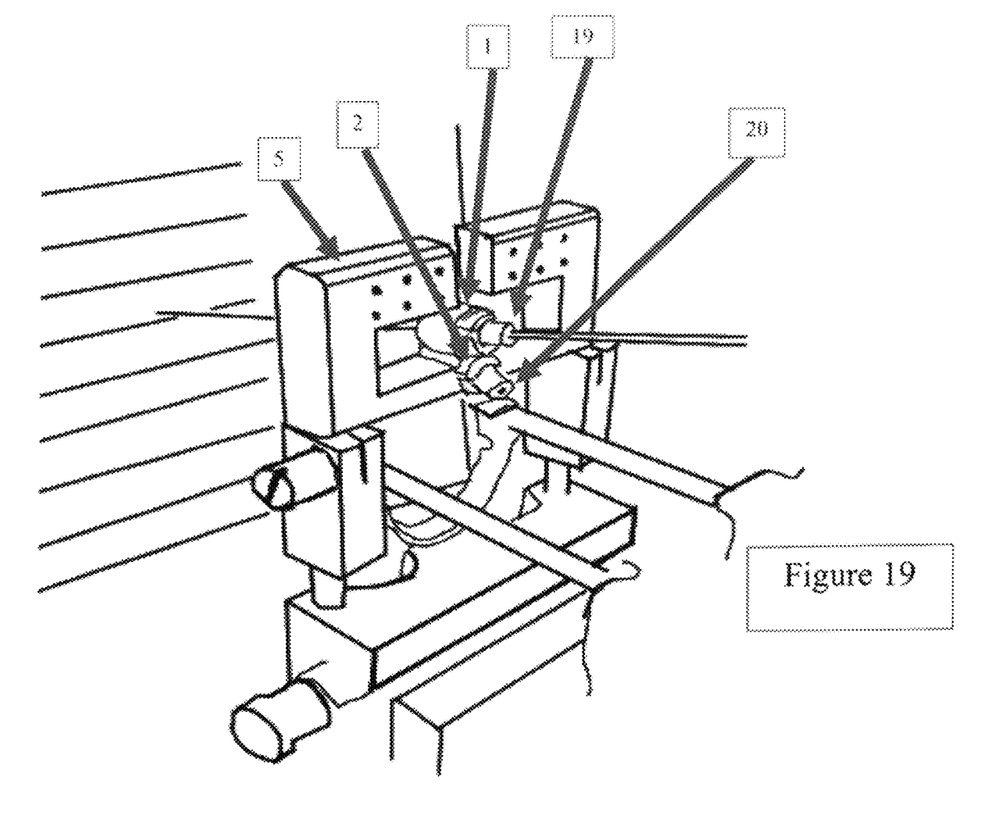
FIG. 19: Template system on representative ultrasound stepper with needle in place through upper variable aperture with needle path angling down.
Figure 20:
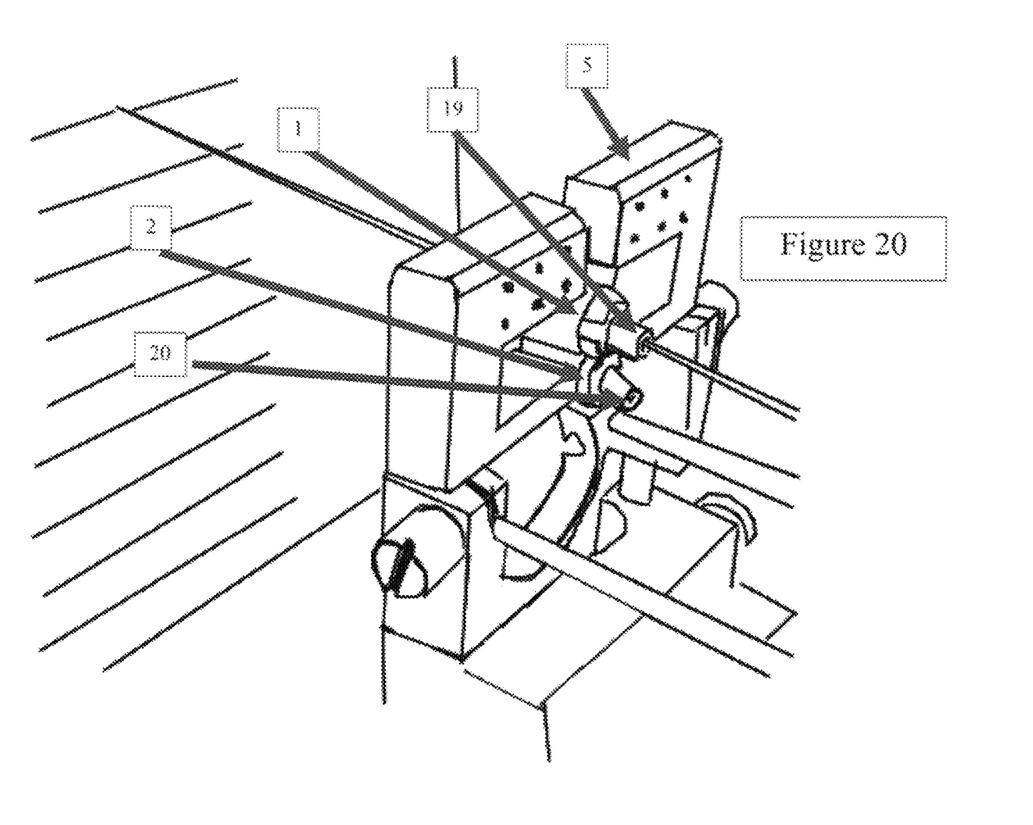
FIG. 20: Template system on representative ultrasound stepper with needle in place through upper variable aperture with needle path angling up.

FIGS. 19 and 20 demonstrate the template system according to the present invention. It is mounted onto a BK stepper unit. In this regard, U.S. Pat. No. 5,931,786A, the contents which are incorporated herein by reference, discloses the endorectal ultrasound stepper system and mounting description of a template grid. A needle traverses the upper central aperture, 19, with FIG. 19 demonstrating the trajectory of the needle pointing downwards and approximating the 4th horizontal line from the top. FIG. 20 demonstrates the same template system with the needle now pointing upwards and approximating the 1st horizontal line from the top demonstrating the ability of a medical implant's trajectory to be adjusted by use of this unique medical invention. Aperture 20 has equal functionality with its site of entrance through the perineum placed more posteriorly.

Figure 21:
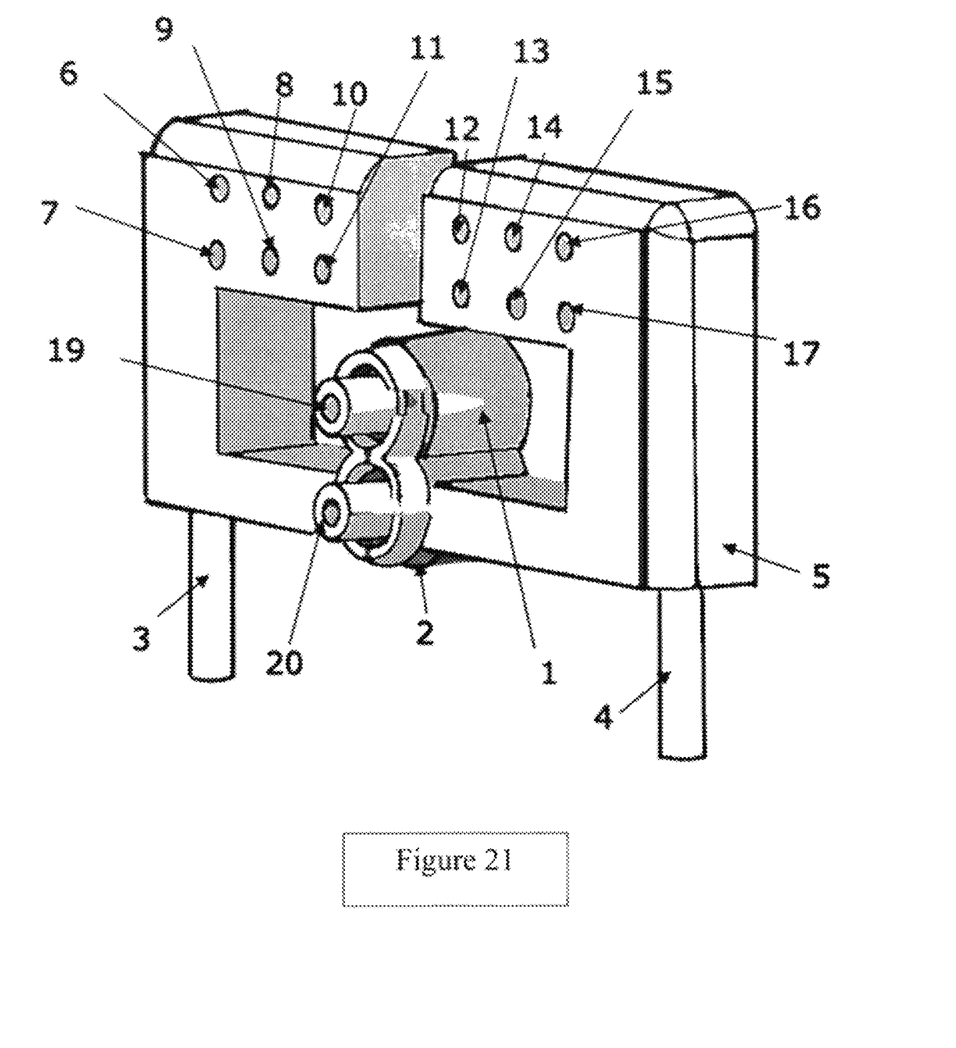
FIG. 21: Oblique view drawing of an embodiment of the template system according to the present invention.

FIG. 21 demonstrates an example of the template system according to the present invention. Apertures labeled 19 and 20 represent central apertures with the ability of rotation within the implant to allow for real time adjustment of the angular trajectory of a medical implant such as a needle or catheter. This is an example of the embodiment of the present invention. These apertures may be designed in different positions within the template system in other examples of the embodiment of the invention to permit entrance of a medical implant such as a needle or catheter through a different position on the perineum where the aperture would allow adjustment of the angular trajectory. For example, apertures 19 and 20 may be placed more superiorly or laterally within the implant to allow the entrance site of a medical implant such as a needle or catheter so that it may permit angular trajectory adjustment, real time.

Within FIG. 21, an example of the embodiment of the present invention, apertures 6 through 17 are fixed apertures which do not permit angular rotation of the trajectory of the medical implant such as a needle or catheter. The apertures are fixed to allow a medical implant to be introduced through the perineum at a fixed angle perpendicular to the surface front plane of the template system. Apertures 12-17 would allow entrance along the left side of midline of the perineum and apertures 6-11 would allow entrance along the right side of midline of the perineum. No apertures are placed at midline to avoid inadvertent placement of a medical implant through the anatomic position of the urethra. No apertures are placed posteriorly to avoid inadvertent placement of a medical implant through the rectum. Apertures 6 and 16 are positioned laterally and anteriorly to allow a medical implant to be placed along a relatively anterior and lateral position of the prostate gland. In contrast, apertures 11 and 13 are positioned to place a medical implant more medially and posteriorly within the prostate gland. Apertures 8 and 14 are positioned more medial to apertures 6 and 16, but at the same anteroposterior position. Apertures 5 and 6 are positioned even more medially but again at the same anteroposterior position as apertures 10 and 12. Aperture 7 and 17 are placed at the same lateral position as apertures 6 and 16 and at the same posterior position of apertures 11 and 13. Apertures 9 and 15 are more medial than apertures 7 and 17, but at the same anteroposterior position. The apertures permit placement of a medical implant into the substance of the prostate gland while safely avoiding the urethra and rectum for purposes such as placement of fiducial markers. Several apertures are available to accommodate varying sizes of prostate glands. This is an example of the embodiment of the present invention. The fixed apertures may be modified on other examples of this embodiment to accommodate different lateral and anteroposterior positions.

| Patent Citations | | | | |
|---|---|---|---|---|
| Publication Number | Priority Date | Publication Date | Assignee | Title |
| US59317867A | 1998 Jun. 11 | 1999 Aug. 3 | Barzell Whitmore Maroon Bells, Inc | Ultrasound probe support and stepping device |
| US6036632A | 1998 May 28 | 2000 Mar. 14 | Barzell Whitmore Maroon Bells, Inc | Sterile disposable template grid system |

SPECIFICATIONS

Figure 1:
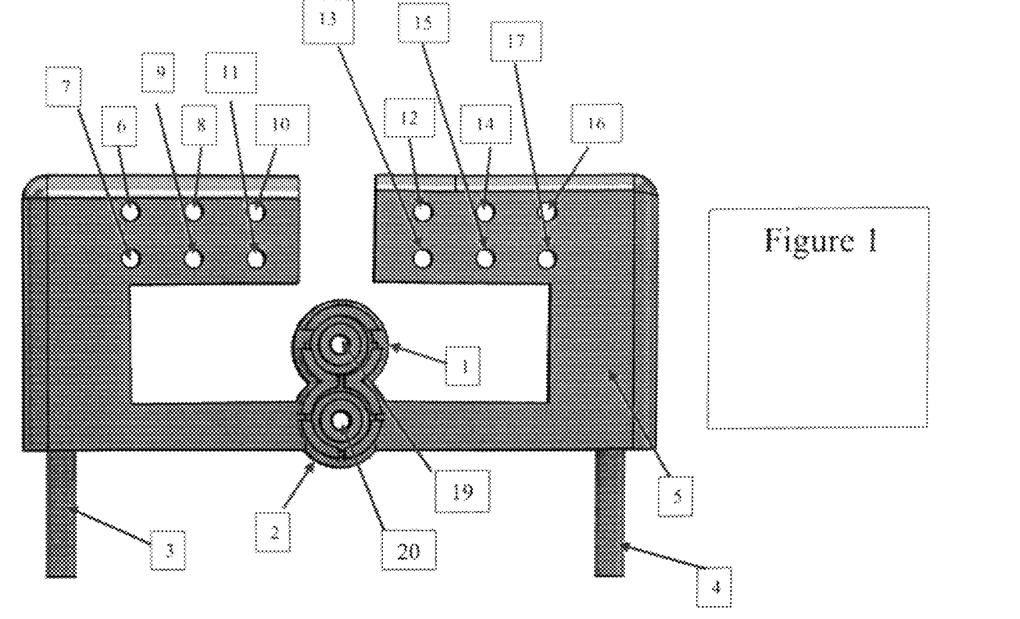
FIG. 1: front view of an embodiment of the template system according to the present invention
Figure 2:
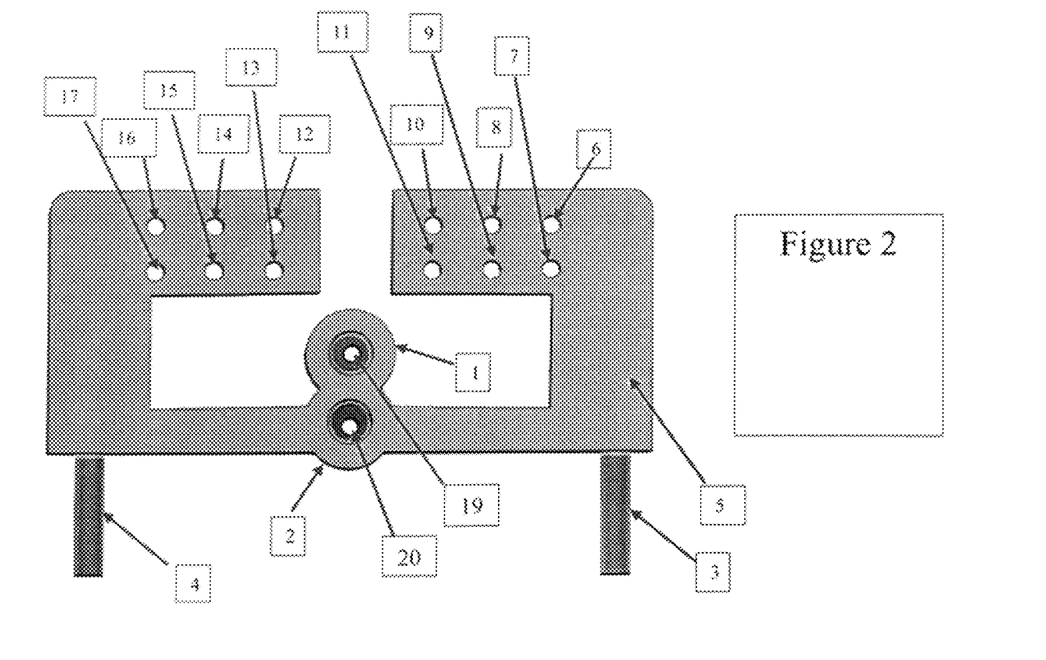
FIG. 2: Rear view of an embodiment of the template system according to the present invention
Figures 3, 4:
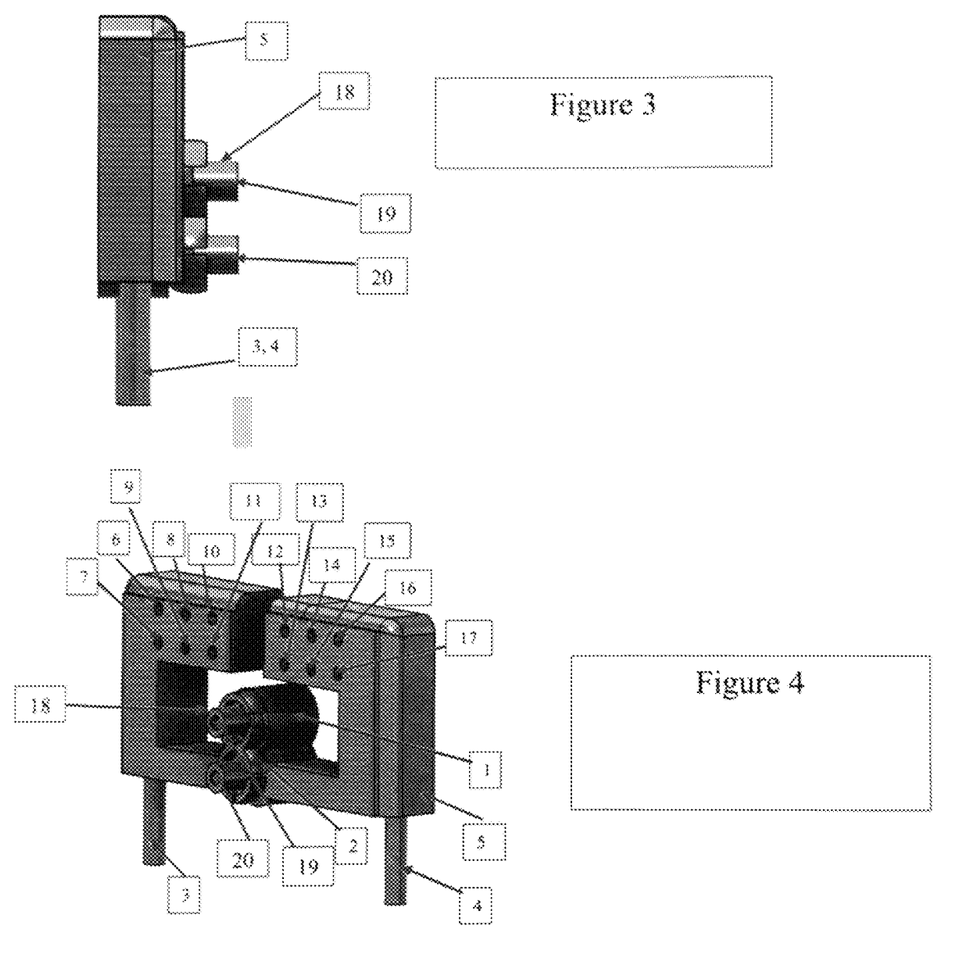
FIG. 3: Side view of an embodiment of the template system according to the present invention
FIG. 4: Oblique view of an embodiment of the template system according to the present invention

Illustration One (1) Description: _embodiment of the template system according to the present invention in FIGS. 1, 2, 3, and 4. FIG. 1 demonstrates a front view. FIG. 2 demonstrates a rear view. FIG. 3 demonstrates a side view and FIG. 4 demonstrates a front oblique view.

Parts and Components Identification

| REFERENCE NUMERAL | PART NAME |
|---|---|
| 1 | Variable angle aperture in FIG. 5, 6, and 7 |

Invention Detailed Description

Description of the Parts of the Invention

| PART NUMBER | PART DESCRIPTION |
|---|---|
| 1 | The variable angle aperture demonstrated in FIG. 5, 6, and 7 allows a medical implant to be placed through its central lumen. Part 1 serves as the ball component of a ball and socket joint with the socket component detailed in part 2. This allows a medical implant such as a needle to be placed with an adjustable trajectory. |

| REFERENCE NUMERAL | PART NAME |
|---|---|
| 2 | Main body |

Invention Detailed Description

Description of the Parts of the Invention

Figure 8:
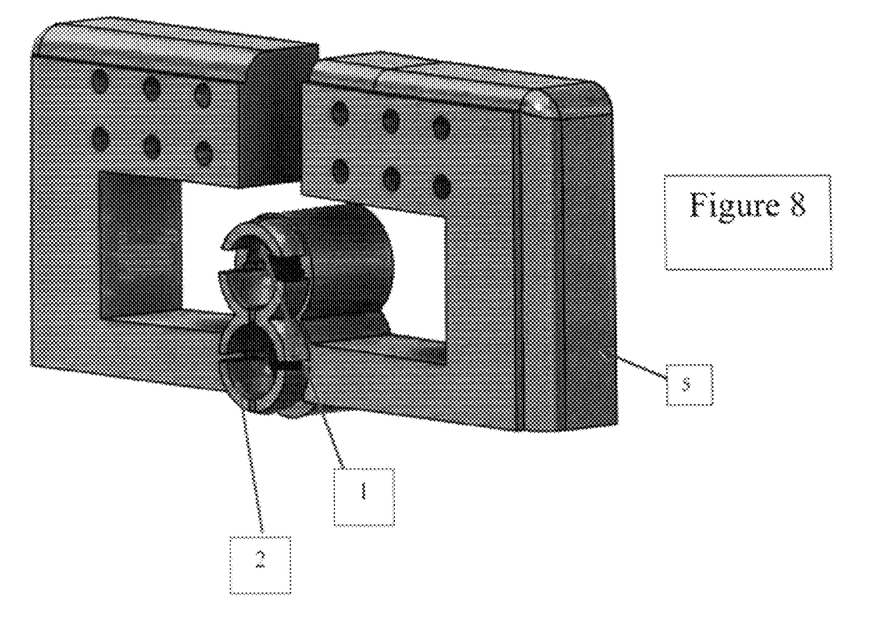
FIG. 8: Body of template demonstrating socket portion which houses ball unit of the device

| PART NUMBER | PART DESCRIPTION |
|---|---|
| 2 | The main body labeled 5 on FIGS. 1, 2, 3, 4, 8, 13, 14, 15, 16, 17, 18, 19, 20, and 21 consists of a central socket component labeled 1 and 2 in FIG. 8 which attaches the ball component of part 1 as demonstrated in FIG. 4 where the socket component labeled 1 and 2 houses the ball component labeled 18. This allows a medical implant to be placed through a lumen in part 1 and rotate along the socket of part 2 to allow for a variable angle of entry for a medical implant. A needle placed through this central lumen is demonstrated in FIGS. 19 and 20. FIGS. 19 and 20 demonstrate the ability of this needle's trajectory to be adjusted. FIGS. 11-18 demonstrate the rotational function of part 1 placed in part 2 for both the upper and lower part 1 units. In addition, the main body consists of fixed apertures labeled 6-17 in FIGS. 1, 2, 4, and 21. These apertures allow passage of a medical implant such as a needle to pass at a fixed trajectory perpendicular to the template grid. This assists in allowing a medical implant such as a needle to be placed laterally away from the urethra and anteriorly away from the rectum to reduce risks of misplacement of a medical implant through these anatomic structures.. |

| REFERENCE NUMERAL | PART NAME |
|---|---|
| 3 | Support Rods |

Invention Detailed Description

Description of the Parts of the Invention

| PART NUMBER | PART DESCRIPTION |
|---|---|
| 3 | 2 Support rods are attached to the bottom of part 2 to allow the template grid to be attached to an ultrasound stepper unit. In this regard, U.S. Pat. No. 5931786A, the contents which are incorporated herein by reference, discloses the endorectal ultrasound stepper system and mounting description of a template grid. The support rods labeled 3 and 4 are demonstrated separately in FIGS. 9 and 10 with a longitudinal and cross view, respectively. The support rods attached to part 2 is demonstrated in FIGS. 1, 2, 3, and 4 and labeled 3 and 4. |

Relationship Between the Parts of the Invention

Two Part 1 ball components attach to the main body, part 2 to complete a ball and socket joint configuration. The socket portion is demonstrated as 1 and 2 in FIG. 8. There are two part number 1 units affixed to part 2 as demonstrated in FIGS. 1, 2, 3 and 4 with FIG. 4 demonstrating part 1 labeled 18 housed in sockets labeled 1 and 2. The stem portion of part 1 faces outward as demonstrated in FIG. 4. This stem portion limits full rotation of the ball and socket joint preventing the central aperture from rotating away from view and access.

Two Part 3 support rods are attached to the main body, part 2 to allow attachment to an ultrasound stepper unit. The support rods are labeled 3 and 4 in FIGS. 1, 2, 3 and 4.

While various embodiments of the present invention are described above, it should be understood that the various features could be used singly or in any combination thereof. Therefore, this invention is not to be limited to only the specifically preferred embodiments depicted herein.

Further, it should be understood that the variations and modifications within the spirit and scope of the invention might occur to those skilled in the art to which the invention pertains. Accordingly, all expedient modifications readily attained by one versed in the art from the disclosure set forth herein that are within the scope and spirit of the present invention are to be included as further embodiments to the present invention. The scope of the present invention is accordingly defined as set forth in the appended claims.

Details of the Invention Operation/Functions

The template grid in the current invention consists of 2 support rods that are positioned to allow attachment to an ultrasound stepper as seen as component 3 and 4 in FIGS. 1, 2, 3, and 4. In this regard, U.S. Pat. No. 5,931,786A, the contents which are incorporated herein by reference, discloses the endorectal ultrasound stepper system and mounting description of a template grid. This allows the template grid to be stabilized in relation to an endorectal ultrasound apparatus. This also allows the template grid to be placed along the surface of the perineal skin. The present invention attached to a BK ultrasound stepper is demonstrated in FIGS. 19 and 20.

The apertures labeled 6-17 in FIGS. 1, 2, 4, and 21 allow for passage of a medical implant through the perineal skin into the substance of the prostate gland with a fixed trajectory positioned away from the anatomic position of the rectum, posteriorly, and urethra, medially. This would provide a safe method of placement of a medical implant such as a needle for placement of fiducial markers and may minimize misplacement and potential injury.

The apertures labeled 19 and 20 in FIGS. 1, 2, 3, 4, and 21 allow passage of a medical implant such as a needle through the perineal skin with an adjustable and variable trajectory for accurate positioning to facilitate placement of a perirectal spacer between the prostate and rectum. Two possible apertures as demonstrated as 19 and 20 in FIGS. 1, 2, 3 4, and 21 provide 2 options of points of entry through the perineal skin which can be chosen by the medical professional based on the patient's anatomy. Both apertures function similarly and allow rotational adjustability of the trajectory of the medical implant for accurate and precise positioning.

Best Manufacturing Method

The template grid represented in FIGS. 1, 2, 3, and 4 can be made by any suitable material. The template grid can be made to be reusable or disposable. In this regard, U.S. Pat. No. 6,036,632, the contents of which are incorporated herein by reference, discloses disposable template grid systems. The template grid system can be sterilized by a method compatible of the material it is produced with and may include options of steam sterilization, gas sterilization, or irradiation.

Unique Features of Invention

The present invention provides unique central apertures that have the ability to rotate to facilitate a variable angle of a medical implant such as a needle. These apertures are attached to a central implant and provide stability of a medical implant. While template grids are currently available, none provide this unique ability of a needle to be placed and its trajectory to be adjusted to precisely place the position of a needle point and maintain its position.

The current invention also facilitates placement of medical implants such as needles into the prostate gland with reduced risks of injury to urethra and rectum by providing fixed trajectory needles placed away from the anatomic location of these two organs. While template grids currently available provide fixed trajectory apertures, none provide limited apertures to limit medical implant from puncturing urethra and rectum.

The invention claimed is:

1. A grid system configured to attach to an ultrasound stepper unit, wherein the grid system comprises:
a front surface;
fixed apertures arranged laterally with respect to a midline of the front surface which facilitate a stable passage of a first medical implant into the prostate gland along a fixed angle trajectory of the first medical implant relative to the front surface;
rotational apertures arranged along the midline of the front surface which facilitate a stable passage of a second medical implant into the perineum to an intended target and which allow a variable angle trajectory of the second medical implant with respect to the front surface,
wherein the first medical implant and the second medical implant each include at least one of a needle or a catheter.

2. The grid system of claim 1, wherein the variable angle trajectory of the second medical implant is along the midline of the front surface.

3. The grid system of claim 1, wherein the rotational apertures are configured to rotate independent of each other.

4. The grid system of claim 1, wherein the fixed angle trajectory of the first medical implant relative to the front surface is 90 degrees.

5. The grid system of claim 1, wherein the first medical implant is configured to deliver a fiducial marker.

6. The grid system of claim 1, wherein the second medical implant is configured to deliver a hydrogel.

7. The grid system of claim 1, further comprising support rods to attach to the ultrasound stepper unit.

8. The grid system of claim 1, wherein the rotational apertures each comprise a ball and a socket.

* * * * *